US012575900B2

(12) United States Patent
Berthet-Rayne et al.

(10) Patent No.: US 12,575,900 B2
(45) Date of Patent: Mar. 17, 2026

(54) STEERABLE EVERSION ROBOT SYSTEM AND METHOD OF OPERATING THE STEERABLE EVERSION ROBOT SYSTEM

(71) Applicant: King's College London, London (GB)

(72) Inventors: Pierre Berthet-Rayne, London (GB); Christos Bergeles, London (GB)

(73) Assignee: King's College London, London (GB)

( * ) Notice: Subject to any disclaimer, the term of this patent is extended or adjusted under 35 U.S.C. 154(b) by 257 days.

(21) Appl. No.: 18/254,735

(22) PCT Filed: Nov. 24, 2021

(86) PCT No.: PCT/GB2021/053059
§ 371 (c)(1),
(2) Date: May 26, 2023

(87) PCT Pub. No.: WO2022/112768
PCT Pub. Date: Jun. 2, 2022

(65) Prior Publication Data
US 2024/0299106 A1     Sep. 12, 2024

(30) Foreign Application Priority Data

Nov. 30, 2020     (GB) ...................................... 2018856

(51) Int. Cl.
*A61B 34/30*     (2016.01)
*A61M 25/01*     (2006.01)
(Continued)

(52) U.S. Cl.
CPC ......... *A61B 34/30* (2016.02); *A61M 25/0119* (2013.01); *B25J 9/065* (2013.01);
(Continued)

(58) Field of Classification Search
CPC .................... B61B 34/30; A61B 34/73; A61B 2034/301; A61B 2017/3435; A61B 2017/00539;
(Continued)

(56) References Cited

U.S. PATENT DOCUMENTS

| | | | |
|---|---|---|---|
| 5,346,498 A * | 9/1994 | Greelis .............. | A61M 25/0119 606/108 |
| 8,986,197 B2 * | 3/2015 | Okada ................ | A61B 1/00133 606/1 |
| 9,282,993 B1 * | 3/2016 | Cohen ................ | A61B 17/3421 |
| 10,954,789 B2 * | 3/2021 | Hawkes .............. | B62D 57/021 |
| 2019/0000429 A1 | 1/2019 | Magana et al. | |
| 2019/0217908 A1 | 7/2019 | Hawkes et al. | |

FOREIGN PATENT DOCUMENTS

| | | |
|---|---|---|
| CN | 110450149 A | 11/2019 |
| DE | 2406823 A1 | 8/1975 |
| WO | 2005/102184 A1 | 11/2005 |

OTHER PUBLICATIONS

Mar. 4, 2022—(WO) International Search Report and Written Opinion—PCT/GB2021/053059.
(Continued)

*Primary Examiner* — Truc M Do
*Assistant Examiner* — Noah W Stiebritz
(74) *Attorney, Agent, or Firm* — Banner & Witcoff, Ltd.

(57) ABSTRACT

The present disclosure relates to an eversion robot system and a method of operating an eversion robot system. In particular, it relates to a steerable eversion robot having a steering structure disposed in its lumen, wherein the steering structure is configured to control a direction of growth of the eversion robot. The eversion robot system of the present invention avoids drag to the surrounding environment while still comprising a mechanism for controlling the direction of growth of the eversion robot for navigating a complex environment.

15 Claims, 11 Drawing Sheets

(51) Int. Cl.
| | |
|---|---|
| *B25J 9/06* | (2006.01) |
| *B25J 9/14* | (2006.01) |
| *A61B 17/34* | (2006.01) |

(52) U.S. Cl.
CPC ....... *B25J 9/142* (2013.01); *A61B 2017/3435*
(2013.01); *A61B 2034/301* (2016.02); *A61M*
*25/0133* (2013.01)

(58) Field of Classification Search
CPC .............. B25J 9/065; B25J 9/142; B25J 9/20;
A61M 25/0113; A61M 25/0119; A61M
25/0133
See application file for complete search history.

(56) References Cited

OTHER PUBLICATIONS

Roboa Ethz, "RoBoa Final Presentation", https://www.youtube.com/watch?v=C256JZx9lrk, Jul. 3, 2020.

Berthet-Rayne Pierre et al., "Mammobot: A Miniature Steerable Soft Growing Robot for Early Breast Cancer Detection", IEEE Robotics and Automation Letters, vol. 6, No. 3, Jul. 2021.

Der Maur Auf Pascal et al., "RoBoa: Construction and Evaluation of a Steerable Vine Robot for Search and Rescue Applications", IEEE 4th International Conference on Soft Robotics, IEEE, Apr. 12, 2021.

May 13, 2021—(GB) Search Report—GB2018856.1.

\* cited by examiner

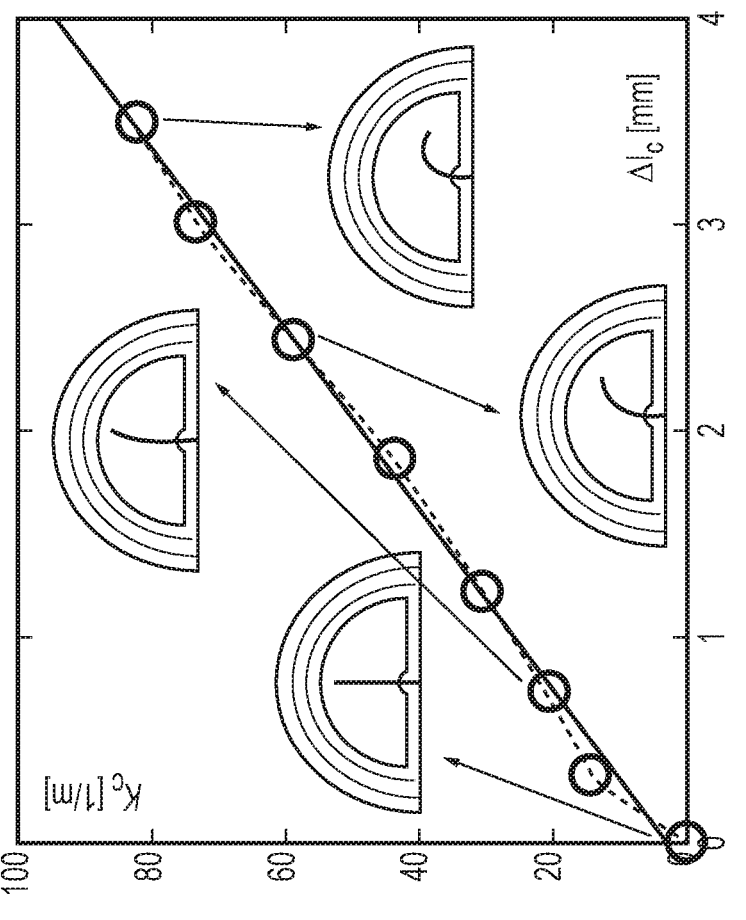
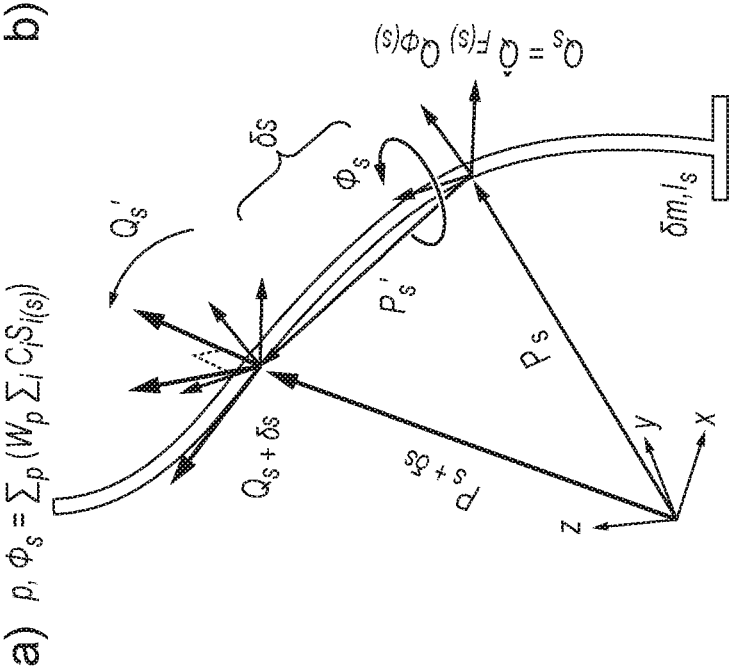
FIG. 4

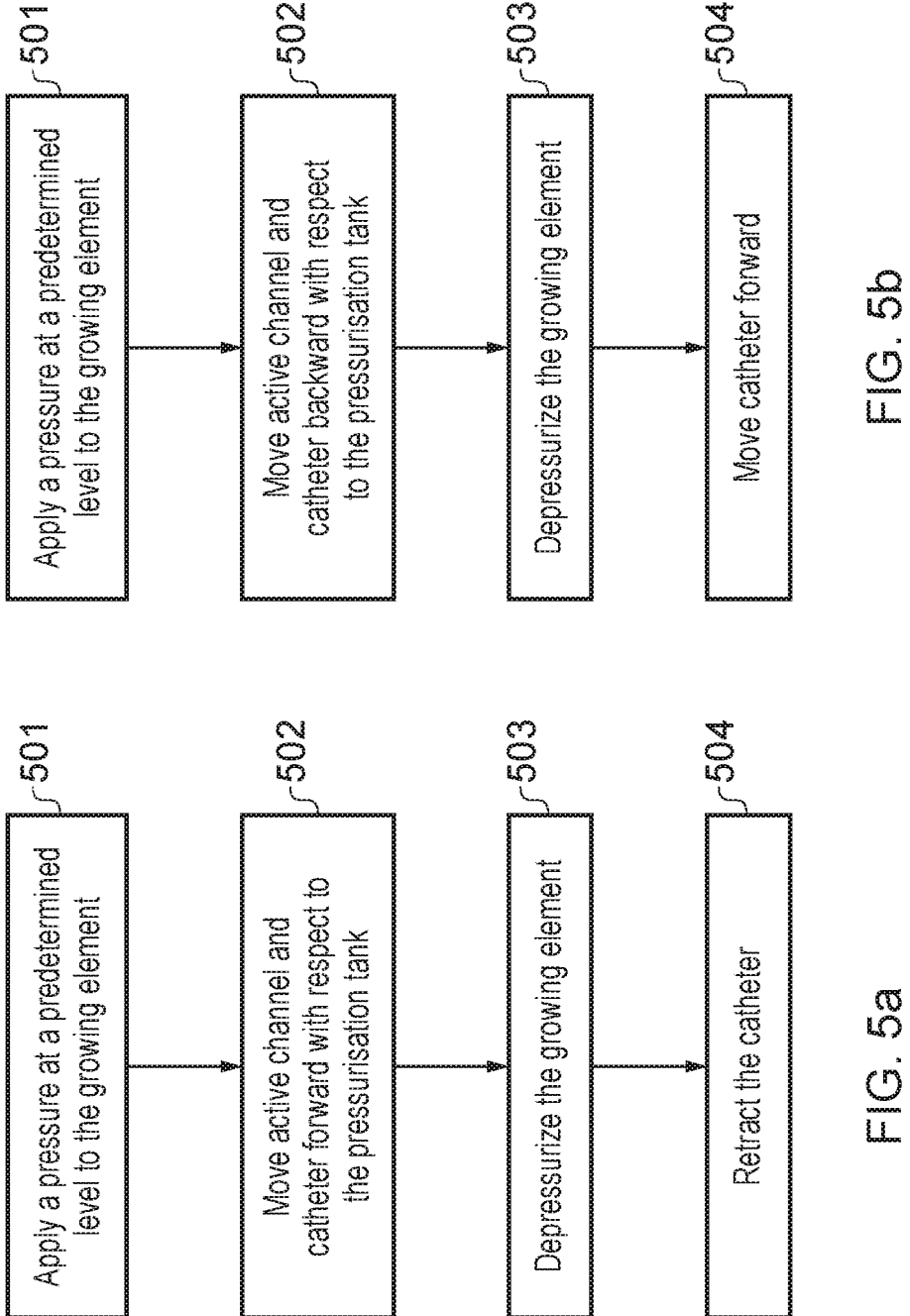

501 Apply a pressure at a predetermined level to the growing element

502 Move active channel and catheter backward with respect to the pressurisation tank 503 Depressurize the growing element 504 Move catheter forward

FIG. 5b

501 Apply a pressure at a predetermined level to the growing element

502 Move active channel and catheter forward with respect to the pressurisation tank 503 Depressurize the growing element 504 Retract the catheter

FIG. 5a

STEERABLE EVERSION ROBOT SYSTEM AND METHOD OF OPERATING THE STEERABLE EVERSION ROBOT SYSTEM

CROSS-REFERENCE TO RELATED APPLICATIONS

This application is a U.S. National Stage application under 35 U.S.C. § 371 of International Application PCT/GB2021/053059, filed Nov. 24, 2021, which claims the benefit of priority to United Kingdom Patent Application GB 2018856.1, filed Nov. 30, 2020. Benefit of the filing date of each of these prior applications are hereby claimed. Each of these prior applications are hereby incorporated by reference in their entirety.

FIELD OF DISCLOSURE

The present disclosure relates to an eversion robot system and a method of operating an eversion robot system. In particular, it relates to a steerable eversion robot having a steering structure disposed in its lumen, wherein the steering structure is configured to control a direction of growth of the eversion robot.

BACKGROUND

Breast cancer cases amount to 55,100 per year in the UK alone and are set to increase both in the UK and worldwide [1]. Early detection of breast cancer, such as Ductal Carcinoma in Situ (DCIS)—Stage 0 breast cancer, is the key to significantly increasing chances of survival. Stage 1 breast cancer has already spread outside of the duct to become Invasive Ductal Carcinoma (IDC). Earlier detection will also reduce the economic burden of treatment, as surgical intervention and chemo radiotherapy will be avoided.

Widespread adoption of mammography has improved the detection of DCIS [2], which now accounts for 25% of detected breast cancers [3]. Mammography only detects DCIS associated with calcifications, and these are less than 50% of DCIS cases [4], [5]. As 80-90% of breast cancers are of intra-ductal origin [6], a tremendous number of cases are missed.

Fibreoptic ductoscopy uses visual cues to detect DCIS while exploring the mammary duct network via the nipple. Despite its potential, the technique has not been widely adopted, simply because current ductoscopy platforms are unwieldy, inflexible, and cannot safely, swiftly and smoothly navigate down the complex tree-like structure of the mammary ducts. Moreover, advancement of the distal end of the ductoscope relies on insertion through pushing, which creates unwanted frictional forces against fragile dilated tissues. Finally, in one study, it was described as taking six months to overcome technical issues to permit routine endoscopy [7].

Soft-growing robots have the potential to re-invent traditional microendoscopic technologies by offering a compelling solution that utilises tip eversion driven by internal pressure [8], [9], [10]. Eversion robots are made from highly compliant materials allowing them to conform to their surrounding environment [11], and delicate anatomy. In addition, as there is no relative motion between the robot and the environment, frictional forces and drag on anatomy walls are minimised.

Previous work on eversion robots has explored materials, actuation approaches and tip-mount designs. Polyethylene (including low density polyethylene (LDPE)) [9], [10], and ripstop fabric (with and without silicone coating) [10], [14], have shown to be prime as eversion materials, as they are almost unstretchable while being flexible and lightweight.

Approaches for active steering include series pneumatic artificial muscles (SPAM) [10], [16], [17], and tendon-stopper mechanisms [13]. These systems decouple extension and steering, which allows for complex geometric shapes to be formed [14]. sPAMs have so far shown promise, but their implementation in medical applications poses challenges related to the requirement of millimetre dimensions. Tendon-stopper mechanisms have not yet been incorporated into fully active steerable systems. Tendons are a scalable alternative, but they must also run along the exterior of the growing robot and hence would be in contact with the lumen during endoscopic applications. Further, they should evert together with the robot's growth, while their actuation may induce friction along the walls of the anatomy.

Tip-mounts are added to eversion robots to transport sensors and tools while remaining at the tip during growth and retraction. Current designs have embodied multiple forms, ranging from outer caps [17], [18], to magnetic rings [15].

WO 2020/060858 discloses a soft everting robot comprising a pressure channel, such that when the channel is pressurized the main body of the everting robot everts. US 2019/0217908 A1 discloses pressure-driven eversion robot configured for navigation. EP 0 913 165 A1 discloses an inverted tube construction for transporting a flexible endoscope shaft. US 2006/173473 A1 discloses an endoscope comprising a longitudinally guiding everting tube.

Given the above, there exists a need for a design of the eversion robot system which provides the advantages of being lightweight, steerable, compliant, avoiding drag to the surrounding environment and permitting multiple working channels during both growing and retraction. While the motivation behind the invention of the present disclosure is to address challenges in medical applications of eversion robot systems, the inventors have also recognised that needs also exist in industrial inspection of narrow corridors and pipes using eversion robot systems, for example in the jet engine industry.

SUMMARY OF DISCLOSURE

The present disclosure provides an eversion robot system to overcome the limitations associated with the above-mentioned prior art eversion robots such as avoiding drag to the surrounding environment while still comprising a mechanism for controlling the direction of growth of the eversion robot.

The proposed eversion robot system of the present invention firstly has the advantage that it maintains a hollow inner lumen throughout its body for enabling the passing of instruments such as miniature endoscopes, biopsy needles and optical probes, depending on the application of the eversion robot. Secondly, it has the advantage of steerability, that is, a control of the direction of growth of the eversion robot. This is enabled by a steerable structure, for example, a steerable catheter which passes through the inner lumen of the eversion robot. In particular, when compared to the prior art as described above, the present invention advantageously enables a minimisation of frictional forces while still providing steerability and growth of the eversion structure. This is particularly beneficial in, for example, endoscopic applications where multi-directional navigation is enabled while minimising friction-induced damage to the anatomy walls.

The proposed eversion robot system of the present invention comprises a growing element having a hollow core, the growing element operable to evert at its distal tip and a means for applying pressure to the growing element. It further comprises a steering means for controlling a direction of growth of the growing element which is provided within the inner core of the growing element.

According to a first aspect of this disclosure, there is provided an eversion robot system comprising: a first tubular structure having a lumen, the first tubular structure arranged to evert and extend at its distal tip; a pressurisation unit arranged to apply a pressure to the first tubular structure; a control structure operable to control the eversion and extension of the first tubular structure; a steering structure operable to navigate the said lumen, wherein the steering structure is configured to control a direction of extension of the first tubular structure, wherein a distal end of the first tubular structure is connected to the pressurisation unit and a proximal end of the first tubular structure is connected to the control structure, and wherein the control structure is configured to enable the insertion of the steering structure into the lumen of the first tubular structure.

According to a second aspect of this disclosure, there is provided a method of operating such an eversion robot system, the method comprising: applying a pressure at a predetermined level on a first tubular structure, the first tubular structure being configured to evert at its tip and extend; moving a control structure in a first direction along a horizontal axis, wherein the control structure is connected to the first tubular structure, wherein the control structure is operable to control the eversion and extension of the first tubular structure; moving a steering structure in the first direction along the horizontal axis at approximately the same time as the control structure, wherein the steering structure is operable to navigate a lumen of the first tubular structure and wherein the steering structure is configured to control a direction of extension of the first tubular structure; reducing the pressure applied on the first tubular structure; and moving the steering structure in a second direction along the horizontal axis, wherein the second direction is opposite to the first direction.

According to a third aspect of this disclosure, there is provided a non-transitory computer-readable medium storing a program causing a computer to operate an eversion robot, the program comprising instructions to: apply a pressure at a predetermined level on a first tubular structure, the first tubular structure being configured to evert at its tip and extend; move a control structure in a first direction along a horizontal axis, wherein the control structure is connected to the first tubular structure, wherein the control structure is operable to control the eversion and extension of the first tubular structure; move a steering structure in the first direction along the horizontal axis at approximately the same time as the control structure, wherein the steering structure is operable to navigate a lumen of the first tubular structure and wherein the steering structure is configured to control a direction of extension of the first tubular structure; reduce the pressure applied on the first tubular structure; and move the steering structure in a second direction along the horizontal axis, wherein the second direction is opposite to the first direction.

According to a fourth aspect of this disclosure, there is provided an eversion robot system comprising: a growing element having a hollow core, the growing element arranged to evert at its distal tip; a means for applying pressure to the growing element; a means for controlling a direction of growth of the growing element, wherein the means for controlling the direction of the growing element is arranged to be disposed in the hollow core of the growing element.

According to another aspect of this disclosure, there is provided an eversion robot system comprising: a growing structure arranged to evert at its distal tip, a first structure, configured to be magnetic in use, coupled to the growing structure, wherein the eversion of the growing structure is enabled by the application of a magnetic field to the first structure.

According to a further aspect of this disclosure, there is provided a method of operating an eversion robot system, the method comprising: applying a magnetic field to a first structure coupled to a growing structure of the eversion robot system to enable the eversion of the growing structure, wherein the growing structure is arranged to evert at its distal tip and wherein the first structure is configured to be magnetic in use.

Further features of the disclosure are defined in the appended claims.

BRIEF DESCRIPTION OF THE DRAWINGS

FIG. 4a shows the spline fitting of a multi-section growing continuum robot with Bishop's curvilinear frame formulation.

FIG. 4b shows experimental results and identified linear relation for the catheter bending curvature vs. tendon pull.

FIGS. 5a and 5b show flow charts for methods of operation for growth and retraction of the eversion robot, respectively, according to embodiments of the present invention.

DETAILED DESCRIPTION

The present disclosure provides an eversion robot for navigation in complex environments using a steering mechanism. The present invention addresses the problem of minimising friction to the environment being navigated while still enabling control in the direction of growth of the eversion robot.

Eversion Robot System

Figure 1A:
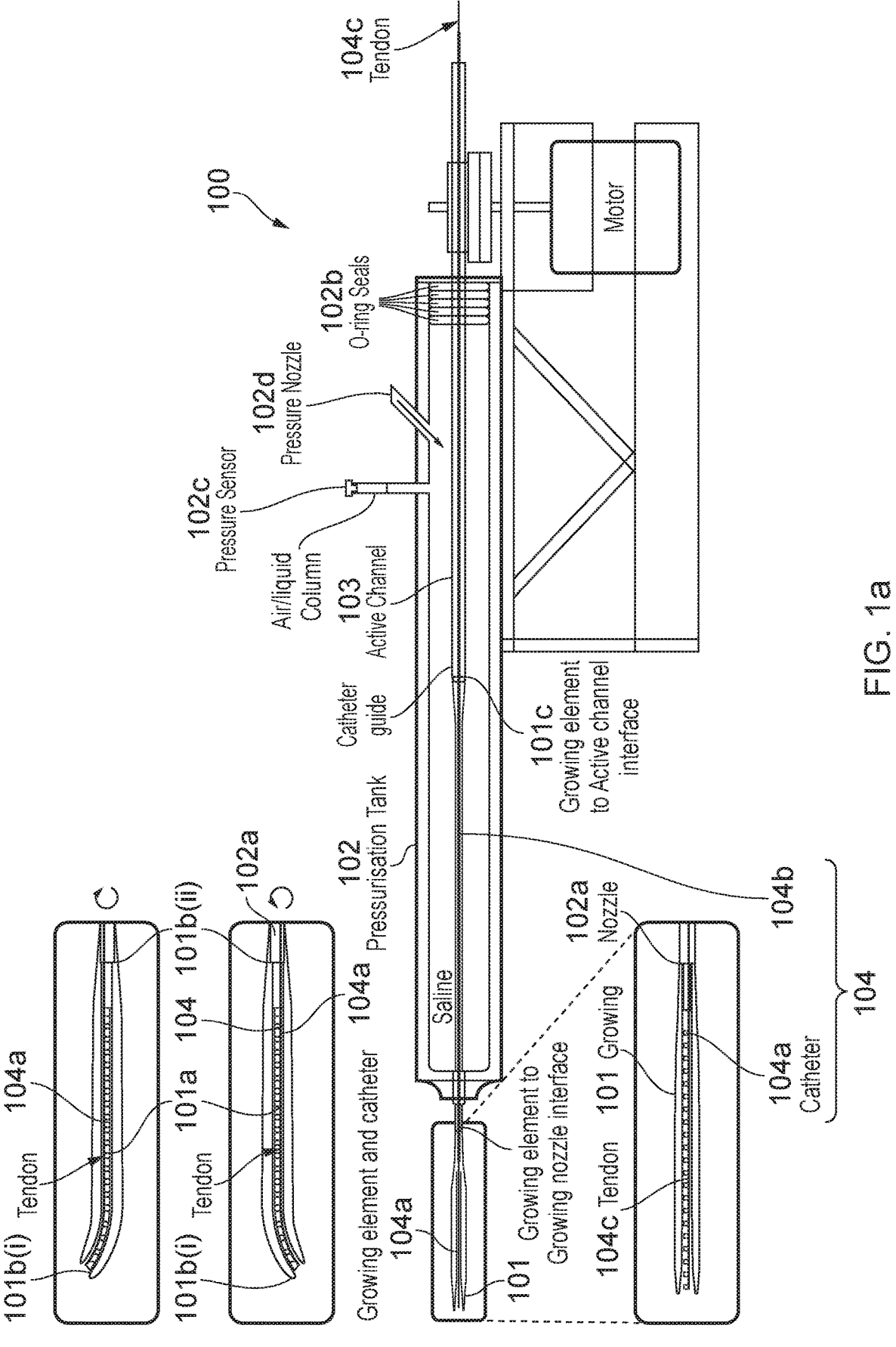
FIG. 1a is a cross-section of an eversion robot system according to an embodiment of the present invention.

FIG. 1a shows a cross-section of an eversion robot system 100 according to an embodiment of the present invention. The eversion robot system comprises a first tubular structure 101 or growing element 101 having a lumen 101a. The first tubular structure 101 is arranged to evert and extend at its distal tip 101b(i). The system also comprises a pressurisation unit 102 arranged to apply a pressure to the first tubular structure 101, a control structure 103 operable to control the eversion and extension of the first tubular structure 101 and a steering structure 104 operable to navigate the said lumen 101a. The steering structure 104 is configured to control a direction of extension of the first tubular structure 101, wherein a distal end 101b(ii) of the first tubular structure is connected to the pressurisation unit and a proximal end 101c of the first tubular structure 101 is connected to the control structure 103, and wherein the control structure 103 is configured to enable the insertion of the steering structure into the lumen of the first tubular structure.

The proposed system comprises a growing robot pressurised with a saline solution, and a robotic catheter 104 responsible for steering. The developed growing robot architecture allows for the control structure 103 or the active inner instrument channel that can be used to pass the robotic catheter, a camera, or other types of instruments such as biopsy needle, snares, or fibreoptic sensors for in situ histopathology and inspection. The robotic catheter 104 is tendon-driven and is inserted through the inner channel 103, enabling robot steering in any direction without hindering growing or retraction.

Growing Element

The growing element 101 of the system is a tube made from 35 μm-thick LDPE film. The tube is everted around itself at the tip as in typical existing growing robot systems and can be seen in FIG. 1. Pressurisation of the robot is achieved with saline solution as opposed to air which is often used in growing robots [8]. The use of saline solution is preferred in clinical applications to prevent the risk of air embolism. The saline solution also presents the advantage of acting as a lubricant as it fills the entire growing element and prevents dry friction during eversion. The growing element is connected to the nozzle 102a of the pressurisation tank on one end, and to the active inner channel tube 103 on the other end.

Figure 1B:
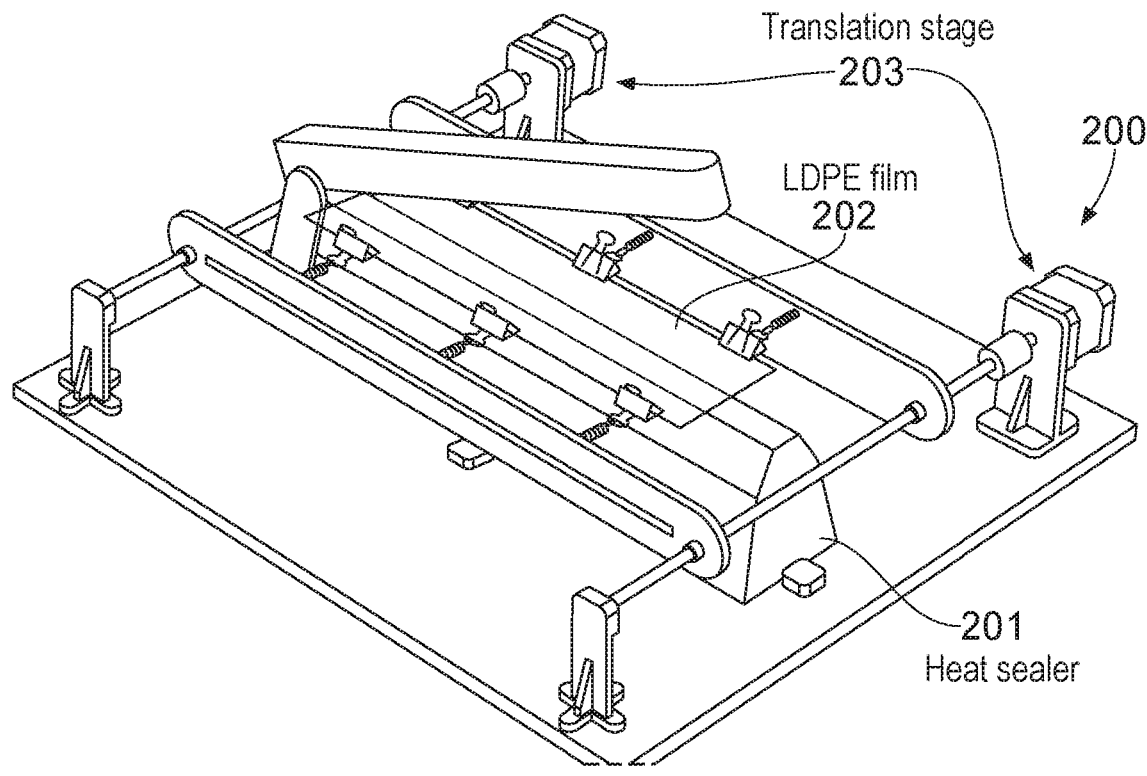
FIG. 1b is a perspective view of a manufacturing rig for the growing element.

The LDPE tube of the growing element 101 was manufactured by welding 2 layers of LDPE film together. To ensure the process' consistency and precision, a bespoke manufacturing rig was designed. The rig consists of an off-the-shelf FS-300 heat sealer, modified with an Arduino Nano to accurately control the welding time, and two T8 3D printer lead screws connected to two Nema 17 stepper motors controlled with A4988 drivers and an Arduino Uno for accurate horizontal translation of two "sandwiched" layers of LDPE film. This enables the repeatable creation of tubular structures of any size with precision. For a 35 μm thick film, the welding time was set to 1600 ms. The precise timing of the welding time is critical; shorter times lead to welds that cannot withstand pressure, while longer welds result in brittle final structures that are prone to micro-leaks. A perspective view of the heat-sealer 201 and the manufacturing rig 200 is shown in FIG. 1b.

The rig 200 was 3D printed with an MK2 in PET-G material. The LDPE film 202 is held onto the translation rig using small clips which are attached to springs to ensure an even tension and a proper alignment. To manufacture a tubular structure of a desired diameter D, the corresponding linear displacement l is calculated based on the perimeter of the tube by $$l = \frac{\pi D}{2} + w \qquad (1)$$

where w is the weld thickness which was characterised during a calibration process. The division by 2 accounts for the two LDPE film layers whose lengths will add up when the tube is inflated. Length l is then converted to motor steps. The developed Arduino firmware allows to adjust with two switches the tube diameter, which is displayed on an LCD screen. Weld commences on user demand with a third switch. To make a complete tube, the operator must first carry out a first weld in-place, and then translate the film and perform the second weld. Finally, the tube is separated from the rig with a paper trimmer that cuts along the external side of the weld.

Pressurisation Tank

The pressurisation tank 102 contains saline solution as pressurisation medium. The tank comprises a 3D printed tubular structure in PET-G material. The tank was made waterproof using acetone dipping and coating. This technique is well suited for FDM printed parts as the acetone will reach within small gaps and locally melt the material acting which then acts as a seal. The tank has a 3 mm stainless steel nozzle 102a on one end (the "growing nozzle"), which connects to the growing structure, and a removable sealed port 102b on the other end, which enables reaching within the tank 102 and improves manoeuvrability during the insertion and manipulation of a new growing element.

Figure 2:
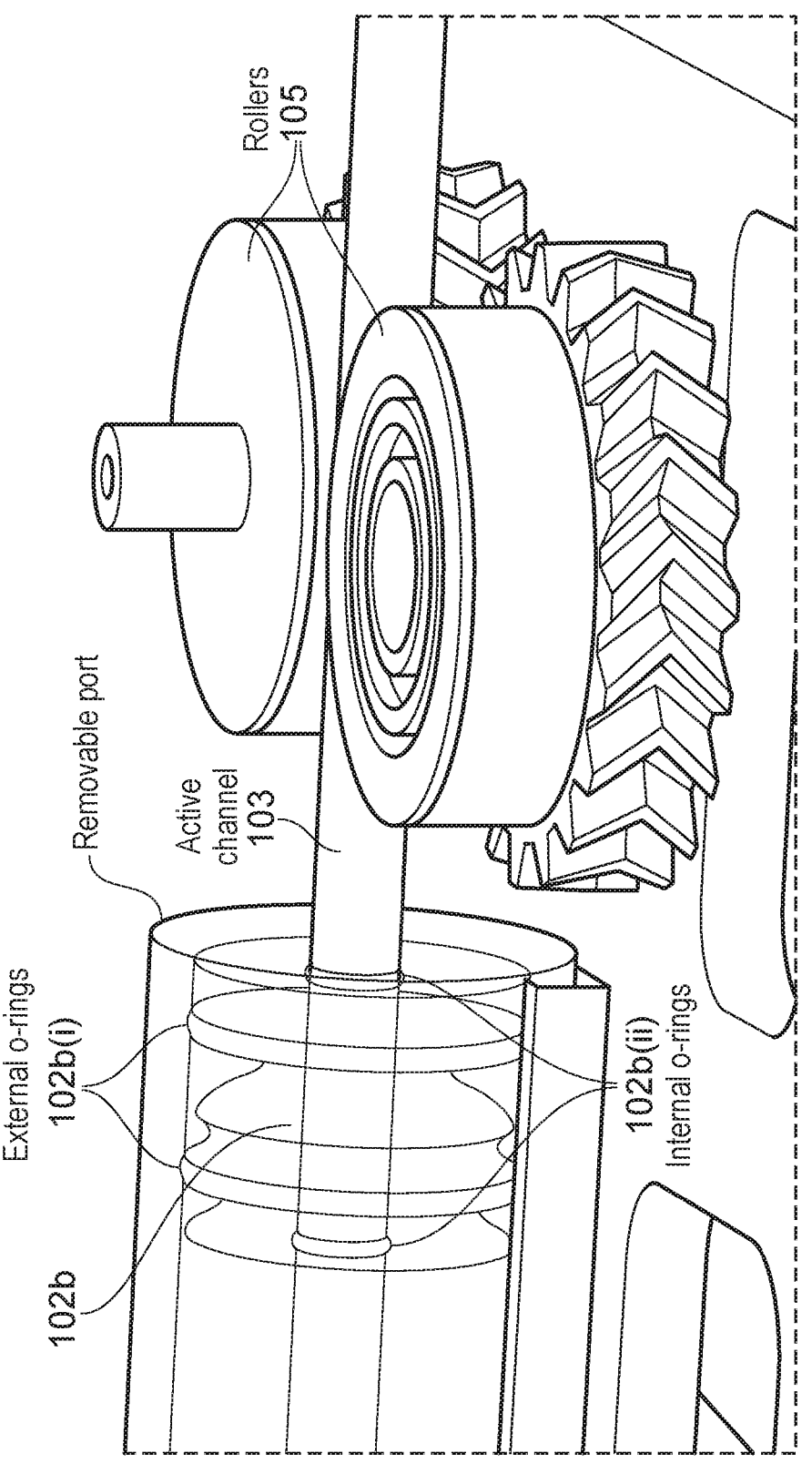
FIG. 2 is a perspective view of the removable portion of the pressurisation unit of the eversion robot system according to an embodiment of the present invention.

FIG. 2 shows a detailed embodiment of the removable sealed port 102b of the eversion robot system of FIG. 1a. The sealed port has a central opening to allow the stainless steel tube 103 of the active instrument channel to slide in and out like the plunger of a syringe. The sealing 102b(i), 102b(ii) between the tank and the cap, as well as the cap and the channel tube, is done with 2 pairs of O-rings as seen in FIG. 2. In other embodiments, the sealing may comprise an arbitrary number of seals. The sealing may also be done with other types of seals such as silicone valves. Finally, the tank has two top nozzles (see FIG. 1a): one small nozzle 102c for pressure measurement with an air/liquid column connected to a pressure sensor as will be described later in more detail, and one large nozzle 102d for hydraulic pressurisation connected to the syringe pump.

Syringe Pump

Pressurisation of the growing element 101 is achieved with a syringe pump (not shown) filled with saline and connected with silicone tubing to the pressurisation tank 102. The syringe pump consists of two Nema 17 stepper motor connected to a pair of T8 lead screws. The lead screws actuate the syringe plunger and are not back-drivable to prevent pressure drop when motors are inert. The pump allows both to pressurise (grow) and depressurise (deflate) the tank.

Two motors are used to maximise the force effected for actuation of the syringe plungers. The pump mechanism was 3D printed in PET-G material. The syringes are off-the-shelf with 10 ml of capacity.

Active Growing Robot Channel

Growing robots can explore confined areas through growth as opposed to insertion, hence limiting the shear forces exerted on the environment. Additionally, growing robots have the intrinsic property to have a hollow core that can be used as an instrument channel or guide. Some work in the literature mentions the potential use of this central channel [8], [24].

However, the inventors have recognised the need for an eversion robot system which enables access of the lumen 101a of the growing robot without interfering with the pressurisation medium. In the present disclosure, the inventors have provided an eversion robot system which enables direct access to the inner channel of a growing robot which can be used, for example, as a catheter. For this purpose, the inventors have proposed the use of an "active channel" 103 as shown in FIG. 1a.

The growing element 101 is connected to the growing nozzle 102a on one end, and to a stainless steel hollow tube, that is, the active channel 103, on the other end. As the growing element 101 is pressurised, eversion is only possible with the simultaneous translation of the active channel 103. The active channel 103 is actuated with two rollers 105 (see FIG. 2) equipped with a thin rubber layer to increase friction. The rollers 105 are synchronously actuated via a pair of Herringbone gears connected to a single Nema 17 stepper motor. A forward motion of the active channel 103 releases the tension of the growing element 101 and enables tip eversion and robot growth. A backward motion of the active channel 103 pulls on the growing element 101 to facilitate its retraction. Pressure increase and decrease should accompany the forward and backward motion of the active channel 103, respectively, to avoid burst of the growing element. This is achieved by a duty cycle controller, which also allows for retraction without buckling, as will be explained in more detail later.

The inventors have recognised that internal pressure on the growing element 101 must be decreased when instruments are to be passed through the inner core. If unregulated, the compressing forces from the sides of the growing element 101 exercise a very large grip that prohibits tool translation.

Catheter and Steering

The proposed solution to steering the eversion robot exploits the active channel 103 and navigates the growing robot from inside with a flexible catheter 104. The steering catheter 104 consists of a 0.94 mm OD flexible NiTi tube 104a, a 0.89 mm OD stainless steel tube 104b and a 0.28 mm 4-strands Dyneema tendon 104c. The respective portions of the steering catheter are also shown in FIG. 1a. The NiTi tube has patterned notches on the side allowing it to bend in a specific direction as the tendon is pulled, similar to [25]. The NiTi tube is attached to a slender stainless steel tube allowing the catheter to travel through the pressurisation tank and reach the tip of the growing element. The catheter is actuated by three stepper motors, 2 Nema 17 for the insertion and roll motion and one Nema 8 to pull the tendon. The stainless steel tube, which is the guiding portion of the catheter, is semi-flexible. The NiTi tube, which is the navigating portion of the steering catheter has patterned notches on the side and is elastic. The navigating portion may also be implemented without any patterned notches while still be able to bend or deflect in a specific direction using a suitable deflecting mechanism. In some other embodiments, depending on the actuation mechanism, the navigating portion need not be elastic nor from NiTi. While a tendon has been implemented in this embodiment, the deflection mechanism for the navigating portion may comprise, for example, a rod or any material that can contract in size by being, for example, piezoelectrically or pneumatically actuated. In some embodiments, the guiding portion may also be fully flexible.

Figure 3:
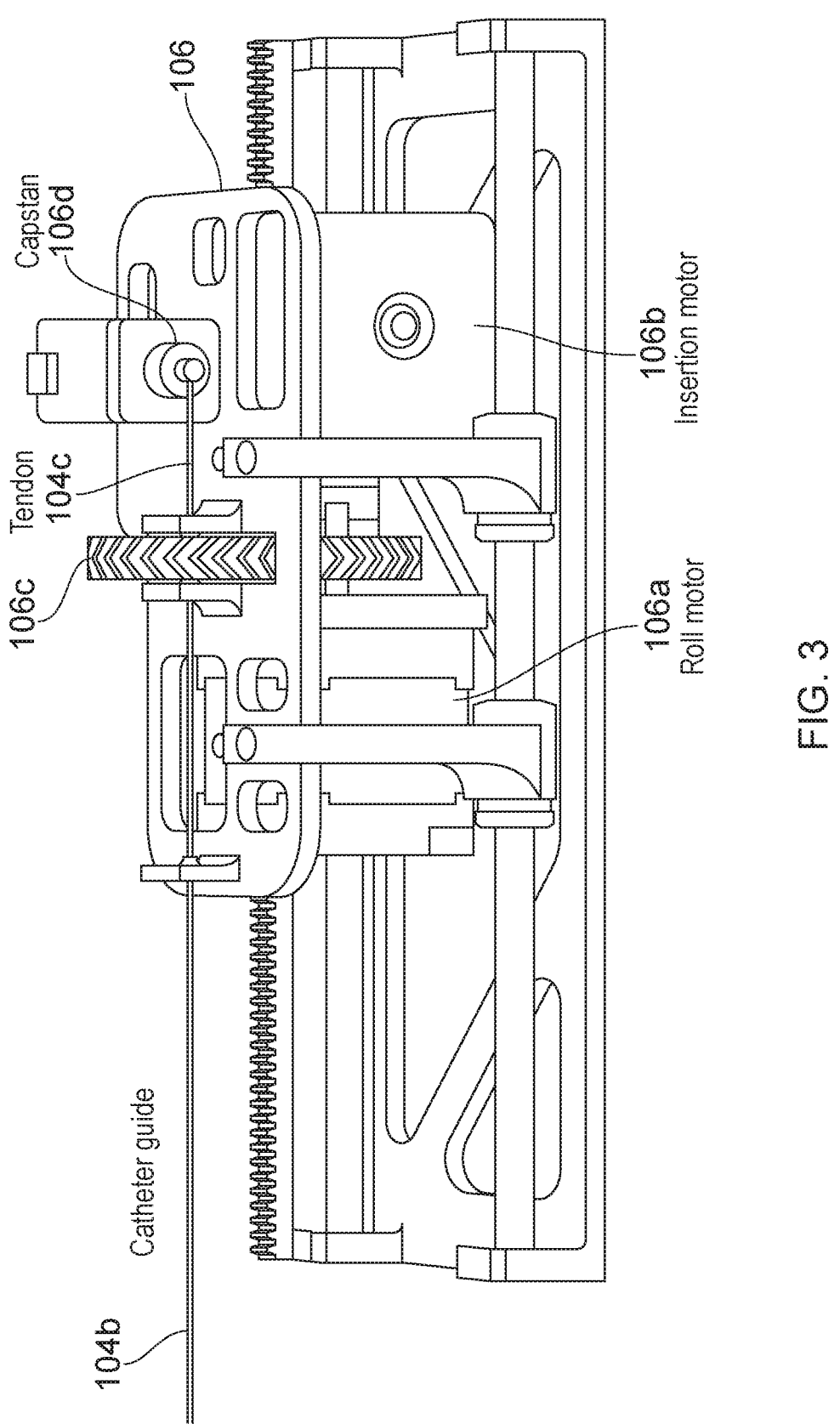
FIG. 3 is a perspective view of an actuator for the steering structure of the eversion robot system according to an embodiment of the present invention.

FIG. 3 provides a more detailed view of an actuator 106 for the catheter 104. By design, the patterned catheter can only bend in one direction. Multi-direction navigation is achieved through the catheter's longitudinal rotation/roll by a pair of Herringbone gears 106c as shown in FIG. 3. The actuation of the tendon 104c is done using a capstan 106d allowing it to wrap around a reel.

System Reduced Order Modelling

Reduced-Order Modelling (ROM) of continuum robots favourably compares to models relying on simplified kinematics (i.e. constant curvature assumption), continuum Cosserat rod methods, and purely learning-based approaches [26]. ROM combines the desirable features of simplicity, accuracy, robustness, and real-time performance, while providing low-dimensional state space for nonlinear controller design [27].

Recently, TMTDyn, a Matlab-based modelling package for ROM of hybrid continuum-rigid body robots, was introduced [26]. TMTDyn features a Domain-Specific Language (DSL) to allow for accessible robot modelling [28]. TMTDyn supported modelling of variable length continuum structures, such as growing robots. We will now describe the ROM dynamics of the eversion robot system implemented using TMTDyn.

As discussed earlier and as shown in FIG. 1a, the eversion robot system comprises three sections: a growing element 101 filled with saline, a tendon-steerable catheter, and a feeding stainless steel tube. The bodies' mass and inertia per unit length are calculated based on the tube dimensions and density $\sigma$, which are either measured or extracted from the literature. The robot backbone ROM kinematics (Cartesian position $p(s)=[x(s),y(s),z(s)]$ and axial twist angle $\phi(s)$) can be captured by four sets (one for each of $x(s)$, $y(s)$, $z(s)$, $f(s)$) of three polynomials (one for each robot section) of order $n_p=3$ with $C^2$-smoothness condition, that is, being twice differentiable at the transition points, as also illustrated in FIG. 4(a).

To capture the backbone multi-section kinematics, a spline of the form:

$$p(s)|\phi(s) = \sum_{p=1}^{3} (W_{p(s)}) \sum_{i=0}^{3} C_{i(t)} s^i \qquad (2)$$

is employed, where $C_i$ are polynomial time variant coefficients (i.e. system Degree of Freedoms—DoFs), s is unit length, and i,p are general numerators. $W_{p(s)}$ are logistic weighting functions of the form $$W_{p(s)} = 1/(1 + e^{200(s-l_p)}) \qquad (3)$$

for continuous transition between the three spline sections with length $l_p$, that is, the axial distance s of every section tip from the robot base (s=0). The spline control points are placed at the end of each robot section, that is, steel tube end $l_{p1}=u_{l1}-l_1$, where $l_1$ is the catheter length, and catheter length $u_{l1}$, which is control input. The robot's length varies due to catheter feeding un and sheath growing $u_{l2}$. The variability is captured by updating the spatial integration range (along robot backbone) of the derived system ROM. A detailed derivation of the system TMT dynamics is provided in [26].

Three translational states are introduced for $p(s)=[x, y, z]$ for which the boundary conditions, that is, backbone base fixed location and right-angle, are enforced and initial conditions (here initially straight) are set. The concentricity constraint (i.e. catheter and growing sheath coaxial motion) is enforced by assigning the same states to construct ROM kinematics of both bodies.

The spatial orientation along the backbone is required for capturing bending, twist, and rotational inertial terms. Frenet-Serret frame derived based on the curve position $p(s)$ cannot capture material twist. A decoupled implementation of the curve quaternion representation of orientation Q(s) may not guarantee the resultant frame to remain curvilinear with respect to the backbone curve [26]. Provided below is a Bishop's frame implementation in TMTDyn which imposes a correction axial rotation $Q_{\varnothing(s)}$ on top of a simplified implementation of a Frenet-Serret frame $Q_{F(s)}$ based on p(s)

$$Q(s) = \hat{Q}_{F(s)} Q_{\varnothing(s)} \tag{4}$$

where $\hat{Q}$ is the skew-symmetric matrix representation of Q. $Q_{\varnothing s}$ base value (s=0) is the body input rotation angle which is fixed for the growing sheath and set as a control input $u_\varnothing$ for the steering catheter.

The bodies' continuum stiffness K and damping p are calculated based on the material modulus of elasticity E and dimensions provided in the literature, the shear modulus $G \approx E/3$, proportional damping $u_{vlu}=0.01K_{vlu}$, and damping power $\mu_p=1$ are considered. Both the growing and catheter bodies are initially straight, that is, $\partial p/\partial s=[0, 0, 1]$ (Cartesian position) and $\partial \kappa/\partial s=[0, 0, 0]$ (curvatures). The tendon length change $\Delta l_c$ governs the initial curvature $\kappa_c$ of the catheter body. The effect of pulling the catheter tendon $\Delta l_c$ is considered as a change in the initial condition for catheter body curvature around initial y-axis $[0, \kappa_c, 0]$.

The inventors performed a set of experiments (see FIG. 4(b)) and identified a linear relation as $\kappa_c=23 \Delta l_c+3.2$. An initial residual curvature of 3.2 1/m is identified as observed in the experiments. It is noted that this relation does not describe the final catheter bent geometry, but predicts the beam curvature initial condition. The final curve shape is determined based on the system governing equations. This relation is used for feedforward estimation of the catheter initial curvature.

A single external load (f, τ) with a variable exertion point along the backbone $l_f$ is considered to model the interaction of the robot with environment. Although a simplistic assumption, it is considered to briefly test the modelling framework. The presented model captures the robot dynamics except for the material motion as the robot sheath grows or catheter feeds. Tendon pulling and catheter base rotations are enforced directly at the kinematic level.

The proposed modelling framework is verified in comparison to an illustrative 2D experiment in the presence of interaction with the environment as will be detailed later in the description. Concordance between the experiments and the model highlight the strong foundation of the proposed framework.

Control & Teleoperation

The control of the eversion robot system of the present invention is divided into three sub-systems: the pump, the growing element, and the catheter. Each sub-system is separately controlled as detailed in the following.

Pressure Control

The pump controls the pressure inside the growing element. The pressure is controlled using a pressure sensor. In one example implementation, the sensor returns an analog differential signal with a 40 mV range. The signal is linearly proportional to the pressure, and the sensor can measure pressures up to 200 kPa. The signal is converted to a digital signal at a sampling rate of 80 Hz. As the pressure sensor is not waterproof, it was interfaced with an air/liquid column approach to prevent direct contact between the medium (saline) and the sensor.

The internal pressure of the growing element 101 is regulated with a PI (Proportional, Integral) controller. The sensor signal is filtered with a moving average filter over 3 samples to reduce signal noise. In this configuration, P was set to 1.1 and I to 0.038. It is important to regulate and control the pressure as it allows a precise and consistent growth of the robot, but it also allows to compensate for pressure variations caused by the insertion/retraction of the active instrument channel. It also prevents any burst of the growing robot as it ensures that pressure remains below a predefined safety threshold.

Robot Control

The proposed robot control concept works as follows: pressure is increased to a set value which induces robot growth. Subsequently, the active channel 103 is pushed forward together with the catheter. Simultaneous actuation of the catheter's roll and bending angles allow to control the direction of robot growth. Several key factors must be considered to make this control approach functional, despite its apparent simplicity.

Growing and Catheter Insertion Rate:

As the active instrument channel 103 is inserted, the growing element 101 will evert new material at its tips and grow. The catheter 104 must follow this motion precisely and synchronously. The growth rate of the growing element, however, corresponds to half the insertion rate of the catheter. An intuitive but under-performing approach to compensate for this behaviour is to move the catheter at half the rate of the growing element. In practice, however, this is not feasible at this scale as the pressure inside the growing element 101 tightly grips the catheter, implying that forceful catheter insertion may lead to material folds, kinks, and even growing element 101 rupture. This is addressed by introducing a duty cycle controller that allows the robot to grow while ensuring that the catheter remains within the lumen of the growing element.

Duty Cycle Controller: The duty cycle controller uses a sequence of commands for safe growth of the robot. Control comprises 4 steps: (G1) Pressurisation to desired (high) pressure; (G2) Channel and catheter synchronous forward motion; (G3) Depressurisation, and (G4) Catheter retraction. This is also shown in FIG. 6 which will be explained in more detail later.

The sequence of steps is continuously repeated during robot elongation, and ensures incremental growth while the catheter remains within the growing element's boundaries. The control algorithm adversely affects robot speed, but brings two key benefits that are usually missing from growing robots. First, having a catheter moving forward within the growing element 101 significantly reduces the pressure required for growth as the catheter actively pushes the everting material forward. Second, during retraction, the catheter acts as a guide that actively pulls the material backwards allowing for retraction the growing robot without buckling. The retraction algorithm follows an inverse pattern of continuously performed steps: (R1) Pressurisation to set (medium) pressure; (R2) Channel and catheter synchronous backward motion; (R3) Depressurisation, and (R4) Catheter forward motion. This is also shown in FIG. 6b.

FIGS. 5a and 5b show flow-charts of methods for operating the eversion robot system of the present invention based on the steps described above.

Figure 6A:
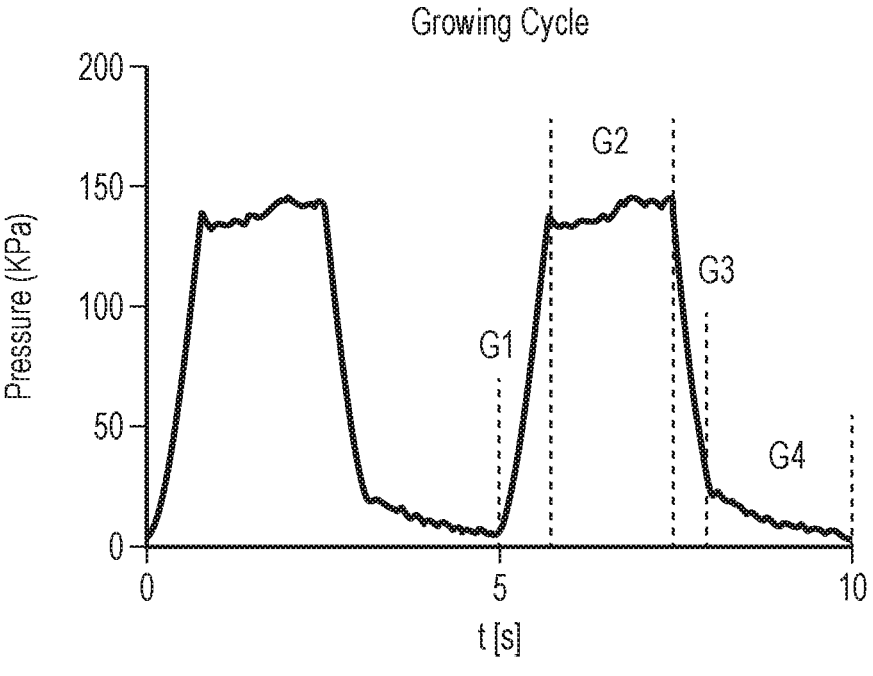
FIG. 6 is a plot of the internal fluid pressure during the growing (FIG. 6a) and retraction (FIG. 6b) phases.
Figure 6B:
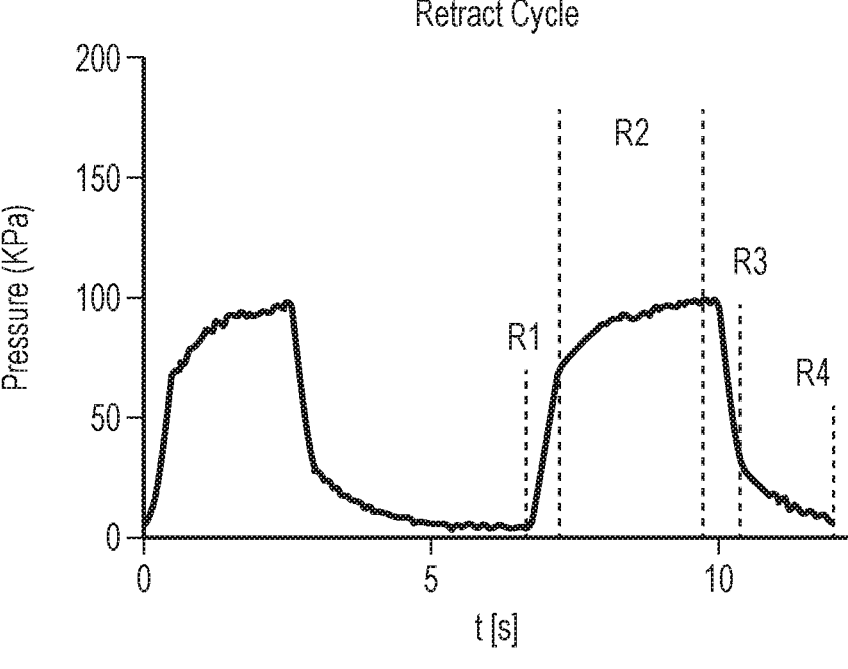

FIG. 6a presents the pressure values for system growth and FIG. 6b presents the pressure values for retraction, in a straight line configuration to evaluate the concept of the duty cycle controller. The growth pressure was set to 140 kPa and the retraction pressure to 100 kPa. The pressure sequences of the duty cycle controller are clearly visible as step functions; the small peak variations correspond to the motion of the active channel 103. Additionally, there is a clear distinction between the growth phase and the retraction phase.

Teleoperation

Teleoperation was performed in a leader-follower configuration with a gamepad controller as the leader device. Gamepad-like controllers are an intuitive way to control catheter-like devices and are starting to appear, for example, in FDA cleared surgical robots. The buttons in such game pads can be used to control robot growth, retraction, duty cycle control and catheter orientation control.

Results and Discussion of Experiments Using the Eversion Robot System

Two sets of experiments were carried out to (1) evaluate the modelling framework, and (2) showcase the navigation capabilities and clinical relevance of the robot.

Model Evaluation in Planar Navigation and Interaction

Figure 8:
FIG. 8 shows images of the insertion of the eversion robot of the present invention in a realistic breast phantom.

The eversion robot is extended to a point that it touches a cubic obstacle and then manoeuvres around it, interacts with it, and retracts as it is sliding against the obstacle. FIG. 8(*a*)-(*d*) presents the input signals, catheter and growing sheath tip location, and sequences of experiments in comparison to the simulation results and animation. The obstacle effect is modelled as a constant external force fe=0.3 N at the contact location If. The simulation results are in good agreement with the experiments with mean distance error of 2.1 mm (4.4% normalised error w.r.t. curve length). The simulations are carried out on a laptop computer with Intel® Core™ i7-8565U 4.4 GHz CPU, 16 GB RAM, and Windows 10 operating system. Simulation time to actual experiment time is currently 4.1×.

Benchtop Navigation

Figure 7:
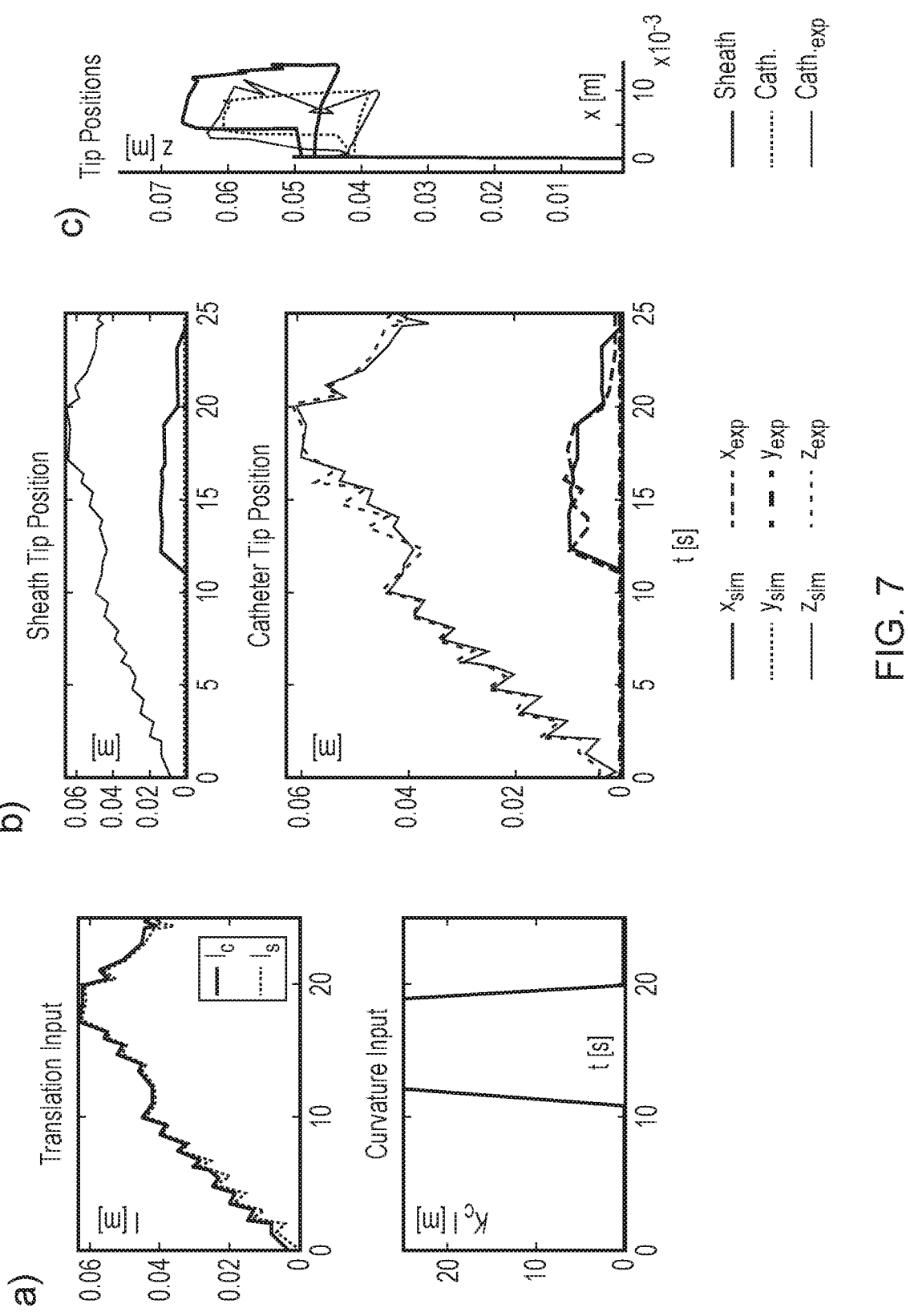
FIG. 7 (a-d) shows the experimental study and modelling verification for a representative navigation task including interaction with environment. (e-f) shows the time-lapse of the navigation of the eversion robot of the present invention.
Figure 7:
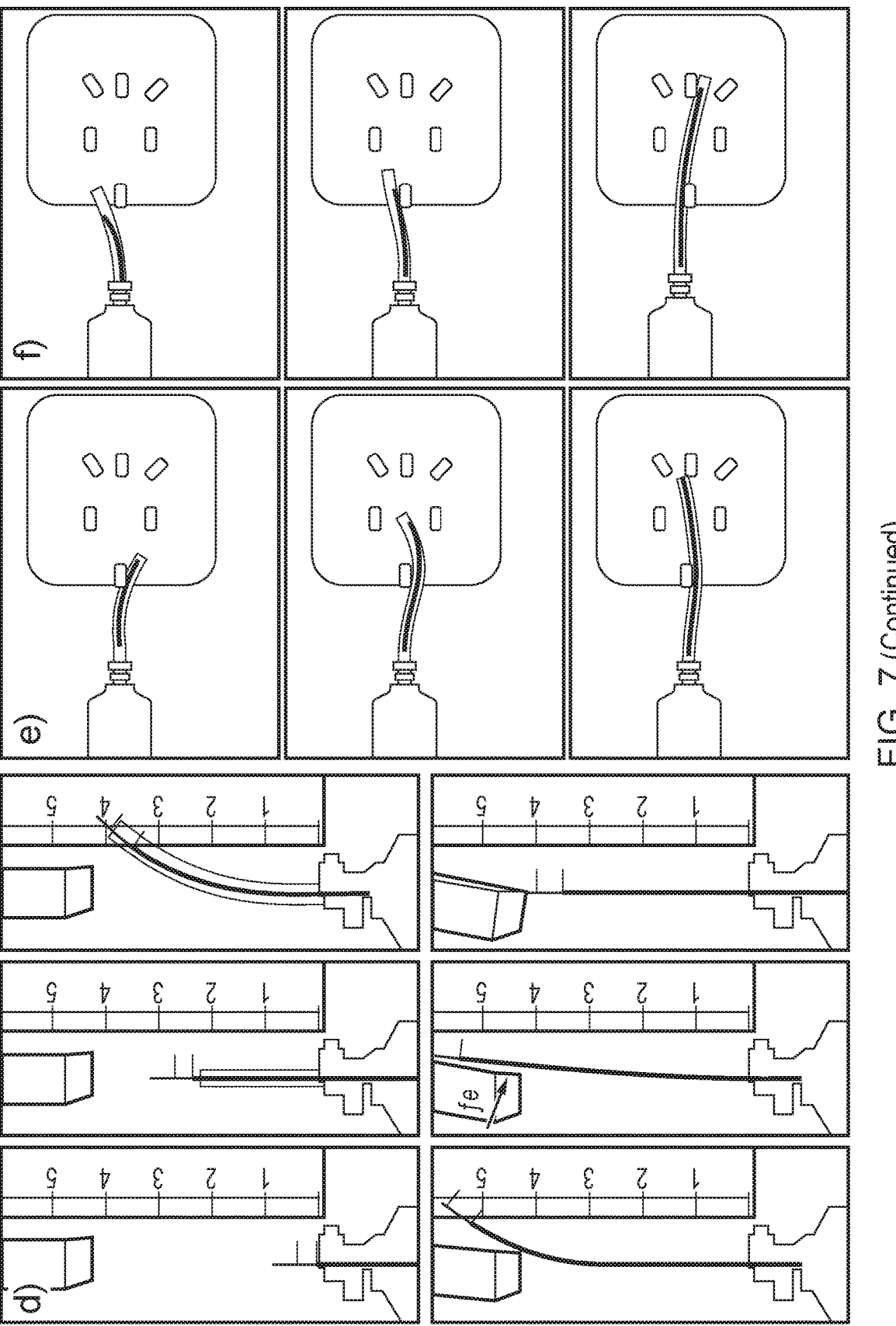

A navigation test rig was 3D printed to test the steering capabilities of the system. The results of the navigation are shown in FIG. 7(*e*)-(*f*). The robot is able to avoid obstacles and follow tortuous path while taking smooth S-shapes.

Navigation Within a Breast Phantom

The inventors have verified the use of the proposed eversion robot system to navigate inside a slightly scaled-up (×1.5) realistic breast phantom. FIG. 8 shows photographs of the navigation in a breast phantom performed with the proposed eversion robot system.

A life-cast of a female adult's breast, a 3D model of the internal breast structures, and 2D anatomical drawings were used as a reference. Through segmentation of the 3D model, a branch of the ductal tree was isolated, and a life-size branch of the ductal tree was 3D printed.

The mould of the breast was created with life casting an adult female breast. The shore 2A platinum silicone was selected to model the skin of the breast. It was pigmented to simulate the colour. The life-like texture was achieved by capturing the live model's skin detail through life-casting. The selected rubber was poured into in the mould to replicate the skin, and the organ in its true dimension, shape, and texture.

When the silicone cured, a plastic base was attached to the skin internally to retain the breast in shape. The breast volume remained hollow. Then the skin (including the plastic base) was demoulded and hand painted to the desired colours.

Subsequently, the ductal tree branch was created by sculpting a magnified version of the 3D printed branch used for reference. The ducts of the branch are of 2-3 mm diameter and each ends into a hollow lobule. The branch was created by a composition of a network of tubes simulating the "negative space" of the internal structure of the ductal tree. Then the sculpted branch was used as a mould to create the ductal branch with shore 2A platinum silicone.

Once the ductal tree was cured, it was pinned onto position on the breast and connected with silicone. The robot could fit within the ductal tree and be removed successfully as shown in FIG. 8.

Figure 9A:
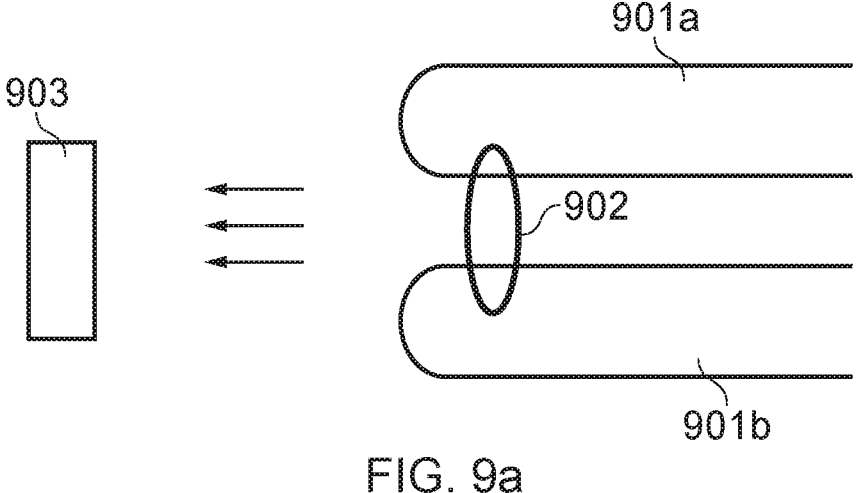
FIGS. 9a-c show another mechanism for eversion of a non-pressurised growing structure of an eversion robot system, according to an embodiment of this disclosure.
Figure 9B:
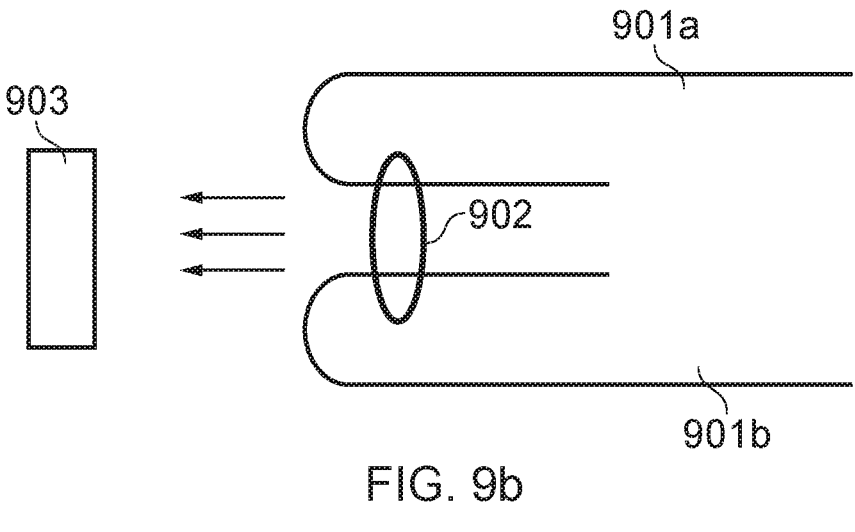
Figure 9C:

FIGS. 9*a-c* shows an example of a further mechanism to control the eversion of the growing element of the eversion robot system, according to another aspect of the present invention.

The inventors have recognised that in eversion robot systems which rely on the use of pressurization for eversion, the material used for eversion is required to be waterproof or airproof depending on the pressurisation medium. The inventors have recognised that this requirement for pressurized growing structures, prevents the use of non-waterproof or non-airproof materials such as fabric-based materials for the growing element. In order to enable the eversion of a non-pressurized growing structure, the inventors have proposed a mechanism as shown in FIGS. 9*a-c*.

The proposed mechanism, as also shown in FIGS. 9*a-c*, comprises the inclusion of a thin ferromagnetic ring or a ring-shaped magnet 902 at the tip of the growing structure 901 within the two folded layers 901*a*, 901*b* of the growing structure. An external magnet 903 is then used to control the growing: that is, as shown by the arrows in FIGS. 9*a* and 9*b*, the external magnet 903 attracts the ferromagnetic ring or the ring-shaped magnet 902, to unfold or evert the growing structure. A segment of the fully everted growing structure is shown in FIG. 9*c*, where the first 901*a* and second 901*b* layers have completely unfolded. The retraction of the growing structure 901 can be performed as in typical growing robots by pulling on the material from the back. Such actuation of growing robots, as described using FIGS. 9*a-9c*, could be used, for example, in medical applications for stent deployment.

Although this invention has been described in terms of certain embodiments, the embodiments can be combined to provide further embodiments. In addition, certain features shown in the context of one embodiment can be incorporated into other embodiments as well.

REFERENCES

[1] CRUK, "Breast cancer statistics." https://bit.ly/31cFLWj, 2020.

[2] K. Kerlikowske, "Epidemiology of ductal carcinoma in situ," JNCI Monographs, vol. 2010, no. 41, pp. 139-141, 2010.

[3] M. van Seijen et al., "Ductal carcinoma in situ: to treat or not to treat, that is the question," British journal of cancer, p. 1, 2019.

[4] B. Barreau et al., "Mammography of ductal carcinoma in situ of the breast: Review of 909 cases with radiographic-pathologic correlations," European Journal of Radiology, vol. 54, no. 1, pp. 55-61, 2005.

[5] F. M. Hall et al., "Nonpalpable breast lesions: recommendations for biopsy based on suspicion of carcinoma at mammography," Radiology, vol. 167, no. 2, pp. 353-358, 1988.

[6] AMC, "Invasive breast cancer." https://bit.ly/3INY1Ny, 2020.

[7] J. S. Simpson et al., "Mammary ductoscopy in the evaluation and treatment of pathologic nipple discharge: a Canadian experience," Canadian Journal of Surgery, vol. 52, no. 6, p. E245, 2009.

[8] E. W. Hawkes et al., "A soft robot that navigates its environment through growth," Science Robotics, vol. 2, no. 8, p. eaan3028, 2017.

[9] L. H. Blumenschein et al., "A tip-extending soft robot enables reconfigurable and deployable antennas," IEEE Robotics and Automation Letters, vol. 3, no. 2, pp. 949-956, 2018.

[10] J. D. Greer et al., "A soft, steerable continuum robot that grows via tip extension," Soft Robot, vol. 6, no. 1, pp. 95-108, 2019.

[11] F. Putzu et al., "Plant-inspired soft pneumatic eversion robot," in IEEE Intl. Conf. on Biomedical Robotics and Biomechatronics, 2018, pp. 1327-1332.

[12] A. Ataka et al., "Model-based pose control of inflatable eversion robot with variable stiffness," IEEE Robotics and Automation Letters, vol. 5, no. 2, pp. 3398-3405, 2020.

[13] D. Rus et al., "Design, fabrication and control of soft robots," Nature, vol. 521, no. 7553, pp. 467-475, 2015.

[14] D. Trivedi et al., "Soft robotics: Biological inspiration, state of the art, and future research," Applied Bionics and Biomechanics, vol. 5, pp. 99-117, 2008.

[15] L. H. Blumenschein et al., "Geometric solutions for general actuator routing on inflated-beam soft growing robots," arXiv preprint arXiv:2006.06117, 2020.

[16] D. A. Haggerty et al., "Characterizing environmental interactions for soft growing robots," in IEEE/RSJ Intl. Conf. on Intelligent Robots and Systems, 2019, pp. 3335-3342.

[17] J. Luong et al., "Eversion and retraction of a soft robot towards the exploration of coral reefs," in 2019 2nd IEEE Intl. Conf. on Soft Robotics, 2019, pp. 801-807.

[18] S.-G. Jeong et al., "A tip mount for transporting sensors and tools using soft growing robots." https://arxiv.org/abs/1912.08297, 2020.

[19] M. Coad et al., "Vine robots: Design, teleoperation, and deployment for navigation and exploration," IEEE Robotics & Automation Magazine, pp. 0-0, 2019.

[20] S. M. Deban et al., "Salamander with a ballistic tongue," Nature, vol. 389, no. 6646, pp. 27-28, 1997.

[21] D. Ramsay et al., "Anatomy of the lactating human breast redefined with ultrasound imaging," Journal of Anatomy, vol. 206, no. 6, pp. 525-534, 2005.

[22] K.-W. Shen et al., "Fiberoptic ductoscopy for breast cancer patients with nipple discharge," Surgical Endoscopy, vol. 15, no. 11, pp. 1340-1345, 2001.

[23] R. Hooper and J. Young, "Media compatibility for ips prt pressure sensors," Freescale Semiconductor, Inc., Tempe, AZ, Tech. Rep., 2008.

[24] P. Slade et al., "Design of a soft catheter for low-force and constrained surgery," in IEEE/RSJ Intl. Conf. on Intelligent Robots and Systems, 2017, pp. 174-180.

[25] P. A. York et al., "A wrist for needle-sized surgical robots," in 2015 IEEE Intl. Conf. on Robot. and Autom. IEEE, 2015, pp. 1776-1781.

[26] S. Sadati et al., "TMTDyn: A Matlab package for modeling and control of hybrid rigid-continuum robots based on discretized lumped systems and reduced-order models," The Intl. Journal of Robotics Research, p. 0278364919881685, January 2020.

[27] C. Della Santina et al., "On an improved state parametrization for soft robots with piecewise constant curvature and its use in model based control," IEEE Robotics and Automation Letters, pp. 1-1, 2020.

[28] S. Sadati et al., "A Matlab-Internal DSL for Modelling Hybrid Rigid-Continuum Robots with TMTDyn," in 6th Workshop on Model-Driven Robot Software Engineering. IEEE, 2019, p. 9.

[29] C. F. Graetzel et al., "Robotic bronchoscopy drive mode of the auris monarch platform," in Int. Conf. on Robot. and Autom., 2019, pp. 3895-3901

The invention claimed is:

1. An eversion robot system comprising:
   a first tubular structure having a lumen, the first tubular structure arranged to evert and extend at its distal tip;
   a pressurisation unit arranged to apply a pressure to the first tubular structure;
   a control structure operable to control the eversion and extension of the first tubular structure;
   a steering structure operable to navigate the said lumen, wherein the steering structure is configured to control a direction of extension of the first tubular structure; and,
   a duty cycle controller configured to coordinate pressurisation of the first tubular structure and eversion and translation of the control structure such that eversion of the first tubular structure occurs only during simultaneous forward motion of the control structure and pressurisation of the first tubular structure;
   wherein a distal end of the first tubular structure is connected to the pressurisation unit and a proximal end of the first tubular structure is connected to the control structure, and
   wherein the control structure is configured to enable the insertion of the steering structure into the lumen of the first tubular structure.

2. An eversion robot system according to claim 1 wherein the steering structure comprises:
   a flexible portion being configured to extend at least partially along the lumen; and
   a means to control the deflection of the said flexible portion.

3. An eversion robot system according to claim 2 wherein the steering structure further comprises a guiding portion configured to be attached to the flexible portion for enabling the movement of the steering structure to the distal tip of the first tubular structure.

4. An eversion robot system according to claim 2 wherein the steering structure comprises a steering catheter and wherein the steering catheter comprises at least one actuable element arranged to control the said deflection of the flexible portion.

5. An eversion robot system according to claim 1, wherein the control structure is at least partially disposed in the pressurisation unit and wherein the control structure is movable along a horizontal axis relative to the pressurisation unit to control the eversion and extension of the first tubular structure.

6. An eversion robot system according to claim 1, wherein one end of the control structure is connected to the proximal end of the first tubular structure and the other end of the control structure is connected to the pressurisation unit.

7. An eversion robot system according to claim 1, wherein the control structure comprises a second tubular structure having an inner channel for guiding the steering structure to enable the insertion of the steering structure into the lumen of the first tubular structure.

8. An eversion robot system according to claim 1, wherein the pressurisation unit comprises a first aperture at a first end and a second aperture at a second end, wherein the second aperture is bound by a sealing structure for enabling insertion of the control structure into the pressurisation unit.

9. An eversion robot system according to claim 1, further comprising an actuator for actuating a movement of the control structure; and/or an actuator for actuating a movement of the steering structure.

10. An eversion robot system according to claim 1, further comprising a controller operable to control the pressurisation of the first tubular structure and a movement of the control structure along a horizontal axis.

11. A method of operating an eversion robot system, the method comprising:

applying a pressure at a predetermined level to a first tubular structure, the first tubular structure being configured to evert at its tip and extend;

moving a control structure in a first direction along a horizontal axis, wherein the control structure is connected to the first tubular structure, wherein the control structure is operable to control the eversion and extension of the first tubular structure and wherein a duty cycle controller configured to coordinate pressurisation of the first tubular structure and eversion and translation of the control structure such that eversion of the first tubular structure occurs only during simultaneous forward motion of the control structure and pressurisation of the first tubular structure;

moving a steering structure in the first direction along the horizontal axis at approximately the same time as the control structure, wherein the steering structure is operable to navigate a lumen of the first tubular structure and wherein the steering structure is configured to control a direction of extension of the first tubular structure;

reducing the pressure applied on the first tubular structure; and moving the steering structure in a second direction along the horizontal axis, wherein the second direction is opposite to the first direction.

12. A method of operating an eversion robot system according to claim 11, wherein the method is for controlling the extension of the first tubular structure and wherein the first direction is a forward direction along the horizontal axis relative to a pressurisation unit of the eversion robot.

13. A method of operating an eversion robot system according to claim 11, wherein the method is for controlling a retraction of the first tubular structure and wherein the first direction is a reverse direction along the horizontal axis relative to a pressurisation unit of the eversion robot.

14. A method of operating an eversion robot system according to claim 13, wherein the said retraction is enabled without buckling of the first tubular structure.

15. A non-transitory computer-readable medium storing a program causing a computer to operate an eversion robot system, the program comprising instructions to:

apply a pressure at a predetermined level on a first tubular structure, the first tubular structure being configured to evert at its tip and extend;

move a control structure in a first direction along a horizontal axis, wherein the control structure is connected to the first tubular structure, wherein the control structure is operable to control the eversion and extension of the first tubular structure and wherein a duty cycle controller configured to coordinate pressurisation of the first tubular structure and eversion and translation of the control structure such that eversion of the first tubular structure occurs only during simultaneous forward motion of the control structure and pressurisation of the first tubular structure;

move a steering structure in the first direction along the horizontal axis at approximately the same time as the control structure, wherein the steering structure is operable to navigate a lumen of the first tubular structure and wherein the steering structure is configured to control a direction of extension of the first tubular structure;

reduce the pressure applied on the first tubular structure; and move the steering structure in a second direction along the horizontal axis, wherein the second direction is opposite to the first direction.

* * * * *